(12) United States Patent
Lebofsky et al.

(10) Patent No.: US 11,834,710 B2
(45) Date of Patent: *Dec. 5, 2023

(54) TRANSPOSASE-BASED GENOMIC ANALYSIS

(71) Applicant: Bio-Rad Laboratories, Inc., Hercules, CA (US)

(72) Inventors: Ronald Lebofsky, Kensington, CA (US); Jennifer Chew, Union City, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 224 days.

This patent is subject to a terminal disclaimer.

(21) Appl. No.: 17/136,824

(22) Filed: Dec. 29, 2020

(65) Prior Publication Data

US 2021/0164036 A1  Jun. 3, 2021

Related U.S. Application Data

(63) Continuation of application No. 16/178,313, filed on Nov. 1, 2018, now Pat. No. 10,907,205.

(Continued)

(51) Int. Cl.
| | |
|---|---|
| *C12Q 1/68* | (2018.01) |
| *C12Q 1/6869* | (2018.01) |
| *C12Q 1/6855* | (2018.01) |
| *C12Q 1/6862* | (2018.01) |
| *C12Q 1/6876* | (2018.01) |
| *C12Q 1/6848* | (2018.01) |
| *C12Q 1/686* | (2018.01) |
| *C12N 15/10* | (2006.01) |

(Continued)

(52) U.S. Cl.
CPC ......... *C12Q 1/6869* (2013.01); *C12N 9/1252* (2013.01); *C12N 15/1003* (2013.01); *C12Q 1/686* (2013.01); *C12Q 1/6806* (2013.01); *C12Q 1/6848* (2013.01); *C12Q 1/6855* (2013.01); *C12Q 1/6862* (2013.01); *C12Q 1/6876* (2013.01); *C12Q 2563/185* (2013.01); *C12Y 207/07007* (2013.01)

(58) Field of Classification Search
CPC ...................................................... C12Q 1/68
USPC ...................................................... 435/6.1
See application file for complete search history.

(56) References Cited

U.S. PATENT DOCUMENTS

| | | |
|---|---|---|
| 5,849,497 A | 12/1998 | Steinman |
| 9,074,251 B2 | 7/2015 | Steemers et al. |

(Continued)

FOREIGN PATENT DOCUMENTS

| | | |
|---|---|---|
| WO | 2010/048605 A1 | 4/2010 |
| WO | 2017/120531 A1 | 7/2017 |

OTHER PUBLICATIONS

Adey, A. et al.; "Rapid, low-input, low-bias construction of shotgun fragment libraries by high-density in vitro transposition"; *Genome Biology*; Biomed Central Ltd.; vol. 11, No. 12; Dec. 8, 2010; 17 pages.

(Continued)

*Primary Examiner* — Aaron A Priest
(74) *Attorney, Agent, or Firm* — Kilpatrick Townsend and Stockton LLP

(57) ABSTRACT

The methods and reagents are provided for barcoding and analysis of DNA samples using partition (e.g., droplet) technology while avoiding performing amplification in droplets.

20 Claims, 9 Drawing Sheets

Specification includes a Sequence Listing.

Related U.S. Application Data

(60) Provisional application No. 62/580,946, filed on Nov. 2, 2017.

(51) Int. Cl.
  *C12N 9/12* (2006.01)
  *C12Q 1/6806* (2018.01)

(56) References Cited

U.S. PATENT DOCUMENTS

| | | | |
|---|---|---|---|
| 2013/0203605 A1* | 8/2013 | Shendure | C12N 15/1093 506/2 |
| 2015/0211055 A1 | 7/2015 | Apte et al. | |
| 2015/0368638 A1 | 12/2015 | Steemers et al. | |
| 2016/0053252 A1 | 2/2016 | Von Hatten et al. | |
| 2016/0369266 A1 | 12/2016 | Belyaev et al. | |

OTHER PUBLICATIONS

Extended European Search Report from EP Appln. 18872646.7 dated Jun. 9, 2021; 6 pages.

Zhang, Fan et al.; "Haplotype phasing of whole human genomes using bead-based barcode partitioning in a single tube"; *Nature Biotechnology*: Advanced Online Publication; Jun. 26, 2017; pp. 1-9.

Amini, Sasan et al.; "Technical Reports—Haplotype-resolved whole-genome sequencing by contiguity-preserving transposition and combinatorial indexing"; *Nature Genetics*; vol. 46, No. 12; Oct. 19, 2014; pp. 1343-1351.

International Search Report and Written Opinion in PCT/US2018/058753 dated Jan. 22, 2019; 15 pages.

Ma, S. et al.; "Chromatin Potential Identified by Shared Single-Cell Profiling of RNA and Chromatin"; *Cell*; vol. 183; Nov. 12, 2020; pp. 1-14.

* cited by examiner

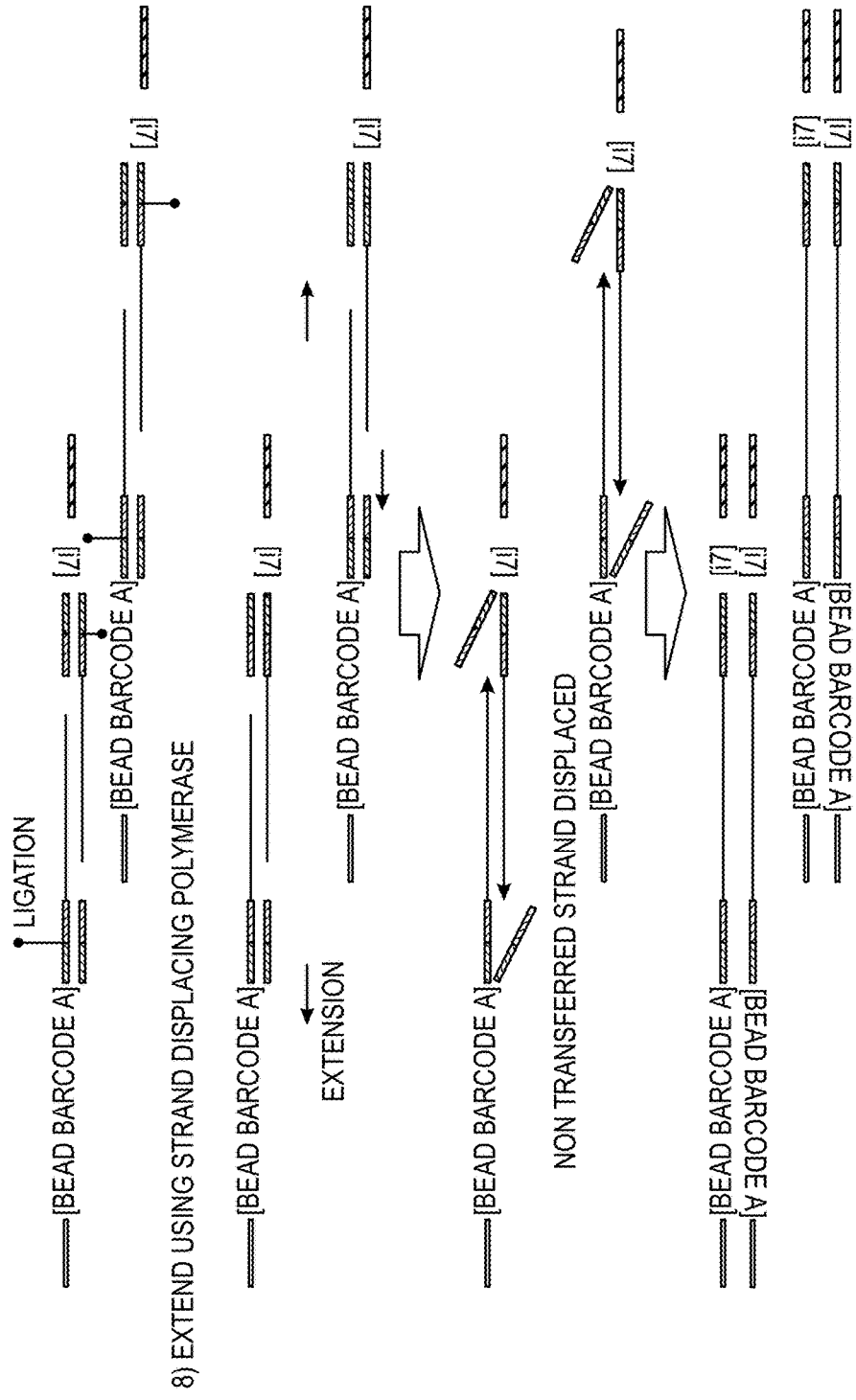

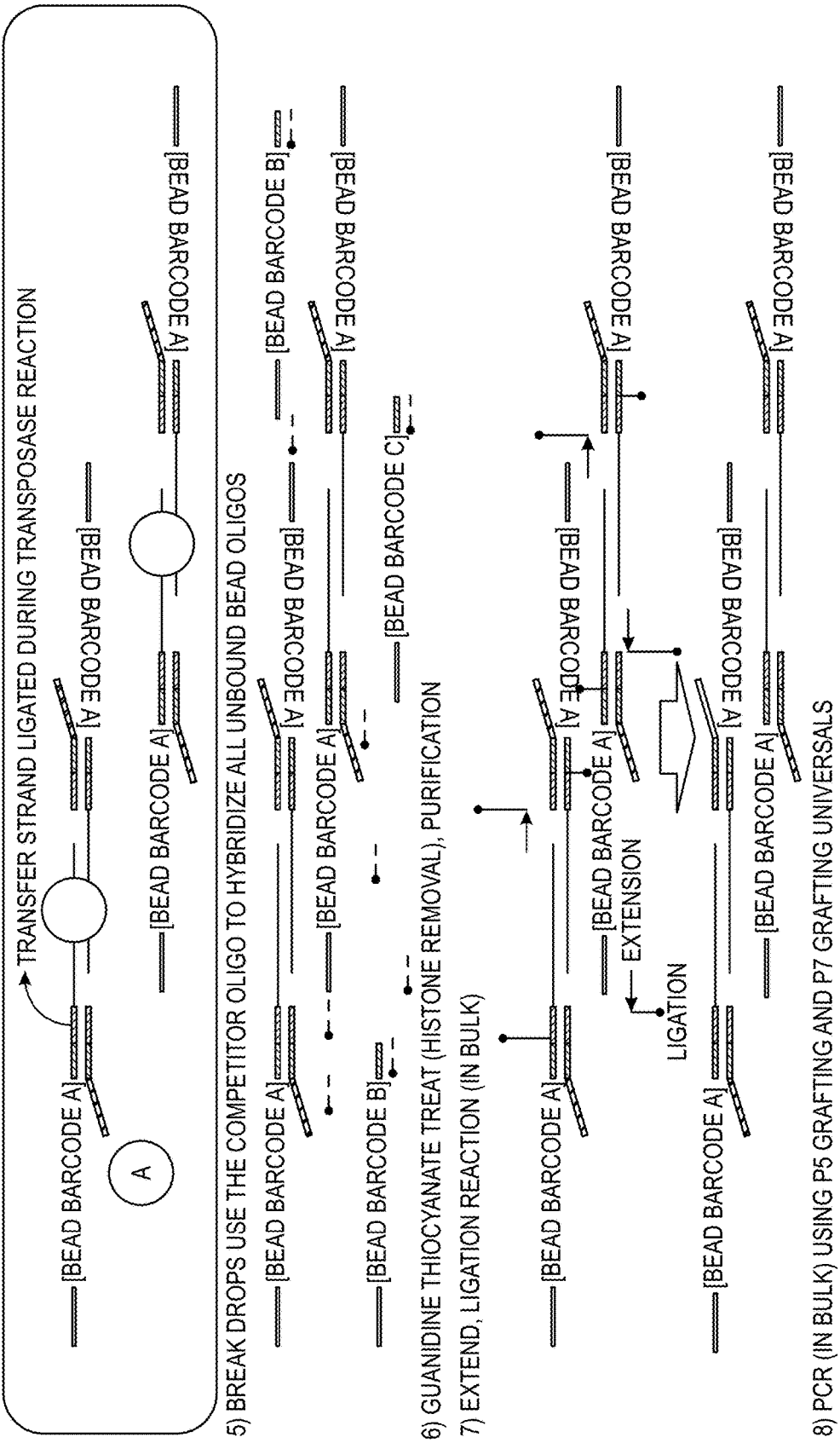

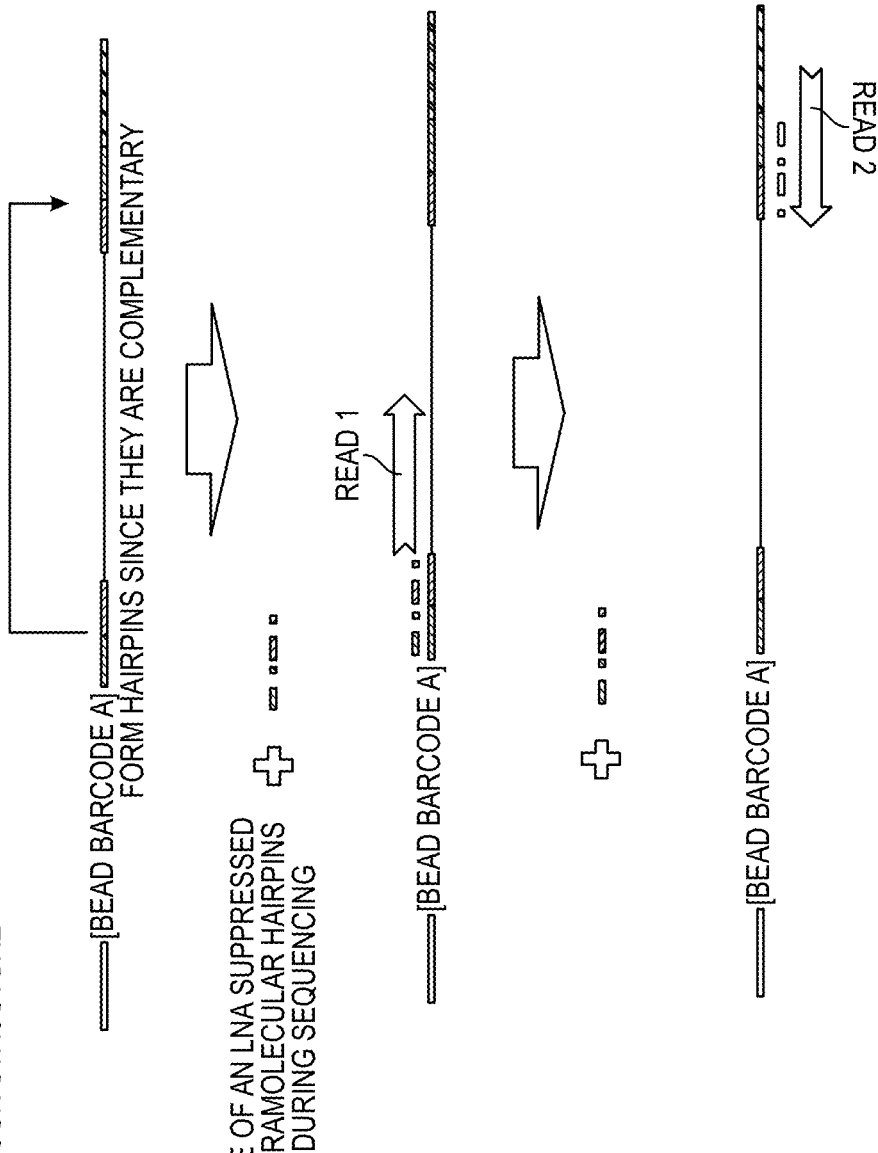

TRANSPOSASE-BASED GENOMIC ANALYSIS

CROSS-REFERENCES TO RELATED APPLICATIONS

The present application is a continuation of U.S. application Ser. No. 16/178,313 filed Nov. 1, 2018, which claims the benefit of U.S. Provisional Appln. No. 62/580,946 filed Nov. 2, 2017, the full disclosures of which are incorporated herein by reference in their entireties for all purposes.

SEQUENCE LISTING

The instant application contains a Sequence Listing which has been submitted electronically in ASCII format and is hereby incorporated by reference in its entirety. Said ASCII copy, created on Dec. 28, 2020, is named 094868-1230395-115920US_SL.txt and is 3,367 bytes in size.

BACKGROUND OF THE INVENTION

Modern sequencing library preparation often involves introduction of a hyperactive variant of the Tn5 transposase that mediates the fragmentation of double-stranded DNA and ligates synthetic oligonucleotides at both ends in a 5-min reaction (Adey A, et al., *Genome Biol* 11: R119 (2010)). Wild-type Tn5 transposon is a composite transposon in which two near-identical insertion sequences (IS50L and IS50R) are flanking three antibiotic resistance genes (Reznikoff W S. *Annu Rev Genet* 42: 269-286 (2008)). Each IS50 contains two inverted 19-bp end sequences (ESs), an outside end (OE) and an inside end (IE). However, wild-type ESs have a relatively low activity and were replaced in vitro by hyperactive mosaic end (ME) sequences. A complex of the transposase with the 19-bp ME is thus all that is necessary for transposition to occur, provided that the intervening DNA is long enough to bring two of these sequences close together to form an active Tn5 transposase homodimer (Reznikoff W S., *Mol Microbiol* 47: 1199-1206 (2003)). Transposition is a very infrequent event in vivo, and hyperactive mutants were historically derived by introducing three missense mutations in the 476 residues of the Tn5 protein (E54K, M56A, L372P), which is encoded by IS50R (Goryshin I Y, Reznikoff W S. 1998. *J Biol Chem* 273: 7367-7374 (1998)). Transposition works through a "cut-and-paste" mechanism, where the Tn5 excises itself from the donor DNA and inserts into a target sequence, creating a 9-bp duplication of the target (Schaller H. *Cold Spring Harb Symp Quant Biol* 43: 401-408 (1979); Reznikoff W S., *Annu Rev Genet* 42: 269-286 (2008)). In current commercial solutions (Nextera DNA kits, Illumina), free synthetic ME adaptors are end-joined to the 5'-end of the target DNA by the transposase.

BRIEF SUMMARY OF THE INVENTION

In some embodiments, methods of barcoding DNA are provided. In some embodiments, the method comprises introducing oligonucleotide adaptors randomly into DNA by contacting the DNA with a transposase loaded with the oligonucleotide adaptors, wherein the oligonucleotide adaptors comprise a 3' single stranded portion and a double stranded portion, with a first oligonucleotide having a 3' end and a 5' end and being a strand of the double-stranded portion and a second oligonucleotide comprising the single-stranded portion and a complementary strand of the double stranded portion, and
wherein the transposase introduces double-stranded breaks into the DNA, wherein each double-stranded break forms two DNA ends and the transposase ligates the first oligonucleotide to one strand of each DNA end, to form DNA fragments comprising the oligonucleotide adaptors at both ends;
forming droplets, wherein the droplets contain the DNA fragments and a first oligonucleotide primer having a bead-specific barcode sequence, wherein the first oligonucleotide primer is linked to a bead and comprises a free 3' end that is complementary to the 3' single stranded portion of the oligonucleotide adaptor;
hybridizing the 3' end of the first oligonucleotide primer (which is optionally released from the bead) to the 3' single stranded portion of the oligonucleotide adaptor;
combining contents of the droplets to form as reaction mixture;
contacting the reaction mixture with a ligase, thereby ligating the first oligonucleotide primer to the 5' end of the first oligonucleotide ligated to the DNA ends, thereby forming barcoded DNA fragments.

In some embodiments, the method further comprises amplifying the barcoded fragments. In some embodiments, the amplifying comprises polymerase chain reaction.

In some embodiments, the method comprises stripping the transposase from the DNA before the hybridizing. In some embodiments, the stripping occurs in the droplets. In some embodiments, the DNA is in a nucleus and the stripping occurs before the forming of the droplets.

In some embodiments, the method comprises cleaving the oligonucleotide primer from beads before the hybridizing.

In some embodiments, the transposase is loaded with two different adaptor oligonucleotides having the same double stranded portion and different single stranded portions.

In some embodiments, the droplets further comprise a second oligonucleotide primer, wherein the second oligonucleotide primer comprises a 3' end sequence at least 50% (e.g., at least 60%, 70%, 80%, 90% or 100%) complementary to one of the single-stranded portions and the first oligonucleotide primer comprises a free 3' end that is at least 50% (e.g., 60%, 70%, 80%, 90% or 100%) complementary to a different 3' single-stranded portion and the hybridizing comprises hybridizing the second oligonucleotide primer to a complementary 3' single-stranded portion. In some embodiments, one single stranded portion comprises GACGCTGCCGACGA (A14; SEQ ID NO:1) and another single stranded portion comprises CCGAGCCCACGAGAC (B15; SEQ ID NO:2).

In some embodiments, the transposase is loaded with two identical adaptor oligonucleotides.

In some embodiments, the first oligonucleotide primer comprises a 5' PCR handle sequence. In some embodiments, the 5' PCR handle sequence of the first oligonucleotide primer comprises AATGATACGGCGACCACCGAGATCTACAC (P5; SEQ ID NO:3). In some embodiments, the droplets further comprise the second oligonucleotide primer and wherein the second oligonucleotide primer comprises a 5' PCR handle. In some embodiments, the 5' PCR handle of the second oligonucleotide primer comprises CAAGCAGAAGACGGCATACGAGAT (P7; SEQ ID NO:4). In some embodiments, the second oligonucleotide primer further comprises an index tag (e.g., barcode).

In some embodiments, the single-stranded portion of the second oligonucleotide comprises:

i. a 3' end sequence less than 50% complementary to the first oligonucleotide primer; and ii. a middle sequence that is at least 50% (e.g., at least 60%, 70%, 80%, 90% or 100%) complementary to the free 3' end of the first oligonucleotide primer.

In some embodiments, the DNA comprises DNA-bound proteins during the introducing. In some embodiments, the method further comprises removing the DNA-bound proteins from the DNA following the combining. In some embodiments, the removing comprising contacting the DNA with a chaotropic agent or protease. In some embodiments, the method further comprises removing the DNA-bound proteins from the DNA before the combining. In some embodiments, the removing comprising contacting the DNA with a chaotropic agent or protease.

In some embodiments, the forming maintains contiguity of the DNA fragments compared to the DNA. In some embodiments, the DNA is purified following the combining and before the contacting.

In some embodiments the method further comprises during the combining, mixing the contents of the droplets with a competitor oligonucleotide comprising the single-stranded portion, which hybridizes to 3' ends of unbound copies of the first oligonucleotide primer, thereby preventing de novo binding of unbound DNA fragments after the combining.

In some embodiments, the method further comprises during the combining, mixing the contents of the droplets with a competitor oligonucleotide comprising the single-stranded portion, which hybridizes to 3' ends of unbound copies of the oligonucleotide adaptors, thereby preventing de novo binding of unbound DNA fragments after the combining.

In some embodiments, the competitor oligonucleotides comprise 3' ends that are not extendable by a polymerase.

In some embodiments, the polymerase in the contacting is a strand displacement polymerase.

In some embodiments, the polymerase in the contacting has 5'-3' exonuclease activity.

In some embodiments, the transposase is a TN5 transposase.

In some embodiments, the transposase is linked to a bead.

In some embodiments, the method further comprises sequencing the barcoded DNA sequences, wherein the sequencing comprises hybridizing and extending a sequencing primer to the barcoded DNA sequences. In some embodiments, the sequencing primer comprises one or more artificial nucleotide that form higher affinity base pairing than occurs in natural nucleotides.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well-known and commonly employed in the art.

The term "amplification reaction" refers to any in vitro means for multiplying the copies of a target sequence of nucleic acid in a linear or exponential manner. Such methods include but are not limited to polymerase chain reaction (PCR); DNA ligase chain reaction (see U.S. Pat. Nos. 4,683,195 and 4,683,202; PCR Protocols: A Guide to Methods and Applications (Innis et al., eds, 1990)) (LCR); QBeta RNA replicase and RNA transcription-based amplification reactions (e.g., amplification that involves T7, T3, or SP6 primed RNA polymerization), such as the transcription amplification system (TAS), nucleic acid sequence based amplification (NASBA), and self-sustained sequence replication (3 SR); isothermal amplification reactions (e.g., single-primer isothermal amplification (SPIA)); as well as others known to those of skill in the art.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing or linear amplification. In an exemplary embodiment, amplifying refers to PCR amplification using a first and a second amplification primer.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Amplification reaction mixtures may also further include stabilizers and other additives to optimize efficiency and specificity. Depending upon the context, the mixture can be either a complete or incomplete amplification reaction mixture "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

A "primer" refers to a polynucleotide sequence that hybridizes to a sequence on a target nucleic acid and serves as a point of initiation of template-based nucleic acid synthesis (for example by primer extension or PCR). Primers can be of a variety of lengths and are often less than 50 nucleotides in length, for example 12-30 nucleotides, in length. The length and sequences of primers for use in primer extension or PCR can be designed based on principles known to those of skill in the art, see, e.g., Innis et al., supra. Primers can be DNA, RNA, or a chimera of DNA and RNA portions. In some cases, primers can include one or more modified or non-natural nucleotide bases. In some cases, primers are labeled.

The term "adaptor" is simply a term to distinguish different oligonucleotides in a mixture. As used herein, "adaptor" is used in the context of oligonucleotides (which may be chemically indistinguishable or not from other oligonucleotides) that have been loaded onto a transposase or that are later ligated to DNA ends by the transposase following transposase fragmentation of the DNA.

A nucleic acid, or a portion thereof, "hybridizes" to another nucleic acid under conditions such that non-specific hybridization is minimal at a defined temperature in a physiological buffer (e.g., pH 6-9, 25-150 mM chloride salt). In some cases, a nucleic acid, or portion thereof, hybridizes to a conserved sequence shared among a group of target nucleic acids. In some cases, a primer, or portion thereof, can hybridize to a primer binding site if there are at least about 6, 8, 10, 12, 14, 16, or 18 contiguous complementary nucleotides, including "universal" nucleotides that are complementary to more than one nucleotide partner. Alternatively, a primer, or portion thereof, can hybridize to a primer binding site if there are fewer than 1 or 2 complementarity mismatches over at least about 12, 14, 16, or 18 contiguous complementary nucleotides. In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 60, 65, 70, 75, or 80° C. In some embodiments, the defined temperature at which specific hybridization occurs is 37, 40, 42, 45, 50, 55, 60, 65, 70, 75, or 80° C. For hybridization to occur, the primer binding site and the portion of the primer that hybridizes will be at least substantially complementary. By "substantially complementary" is meant that the primer binding site has a base sequence containing an at least 6, 8, 10, 15, or 20 (e.g., 4-30, 6-30, 4-50) contiguous base region that is at least 50%, 60%, 70%, 80%, 90%, or 95% complementary to an equal length of a contiguous base region present in a primer sequence. "Complementary" means that a contiguous plurality of nucleotides of two nucleic acid strands are available to have standard Watson-Crick base pairing. For a particular reference sequence, 100% complementary means that each nucleotide of one strand is complementary (standard base pairing) with a nucleotide on a contiguous sequence in a second strand.

A "template" refers to a polynucleotide sequence that comprises the polynucleotide to be amplified, flanked by or a pair of primer hybridization sites. Thus, a "target template" comprises the target polynucleotide sequence adjacent to at least one hybridization site for a primer. In some cases, a "target template" comprises the target polynucleotide sequence flanked by a hybridization site for a "forward" primer and a "reverse" primer.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot) or another moiety.

A "polymerase" refers to an enzyme that performs template-directed synthesis of polynucleotides, e.g., DNA and/or RNA. The term encompasses both the full length polypeptide and a domain that has polymerase activity. DNA polymerases are well-known to those skilled in the art, including but not limited to DNA polymerases isolated or derived from *Pyrococcus furiosus, Thermococcus litoralis*, and *Thermotoga maritime*, or modified versions thereof. Additional examples of commercially available polymerase enzymes include, but are not limited to: Klenow fragment (New England Biolabs® Inc.), Taq DNA polymerase (QIAGEN), 9° N™ DNA polymerase (New England Biolabs® Inc.), Deep Vent™ DNA polymerase (New England Biolabs® Inc.), Manta DNA polymerase (Enzymatics®), Bst DNA polymerase (New England Biolabs® Inc.), and phi29 DNA polymerase (New England Biolabs® Inc.).

Polymerases include both DNA-dependent polymerases and RNA-dependent polymerases such as reverse transcriptase. At least five families of DNA-dependent DNA polymerases are known, although most fall into families A, B and C. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

As used herein, the term "partitioning" or "partitioned" refers to separating a sample into a plurality of portions, or "partitions." Partitions are generally physical, such that a sample in one partition does not, or does not substantially, mix with a sample in an adjacent partition. Partitions can be solid or fluid. In some embodiments, a partition is a solid partition, e.g., a microchannel. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

As used herein a "barcode" is a short nucleotide sequence (e.g., at least about 4, 6, 8, 10, 12, 15, 20, or 50 nucleotides long or more) that identifies a molecule to which it is conjugated. Barcodes can be used, e.g., to identify molecules in a partition. Such a partition-specific barcode should be unique for that partition as compared to barcodes present in other partitions. For example, partitions containing target RNA from single-cells can be subject to reverse transcription conditions using primers that contain different partition-specific barcode sequence in each partition, thus incorporating a copy of a unique "cellular barcode" into the reverse transcribed nucleic acids of each partition. Thus, nucleic acid from each cell can be distinguished from nucleic acid of other cells due to the unique "cellular barcode." In other examples, partitions containing CPT-DNA can be subject to PCR conditions using primers that contain different partition-specific barcode sequences in each partition, thus incorporating a copy of a unique CPT-DNA barcode into the PCR amplicons of each partition. Substrates can be cellular RNA, cellular DNA and/or long contiguous DNA molecules. In some cases, substrate barcode is provided by a "particle barcode" (also referred to as "bead-specific barcode") that is present on oligonucleotides conjugated to a particle, wherein the particle barcode is shared by (e.g., identical or substantially identical amongst)

all, or substantially all, of the oligonucleotides conjugated to that particle. Thus, substrate and particle barcodes can be present in a partition, attached to a particle, or bound to cellular nucleic acid as multiple copies of the same barcode sequence. Substrate or particle barcodes of the same sequence can be identified as deriving from the same substrate (e.g., a long DNA molecule that has been cleaved but maintains contiguity), cell, partition, or particle.

In other cases, barcodes uniquely identify the molecule to which it is conjugated. For example, by performing reverse transcription using primers that each contain a unique "molecular barcode." In still other examples, primers can be utilized that contain "partition-specific barcodes" unique to each partition, and "molecular barcodes" unique to each molecule. After barcoding, partitions can then be combined, and optionally amplified, while maintaining virtual partitioning. Thus, e.g., the presence or absence of a target nucleic acid (e.g., reverse transcribed nucleic acid) comprising each barcode can be counted (e.g. by sequencing) without the necessity of maintaining physical partitions.

The length of the barcode sequence determines how many unique samples can be differentiated. For example, a 1 nucleotide barcode can differentiate 4, or fewer, different samples or molecules; a 4 nucleotide barcode can differentiate $4^4$ or 256 samples or less; a 6 nucleotide barcode can differentiate 4096 different samples or less; and an 8 nucleotide barcode can index 65,536 different samples or less. Additionally, barcodes can be attached, for example, through ligation or in a transposase reaction.

Barcodes are typically synthesized and/or polymerized (e.g., amplified) using processes that are inherently inexact. Thus, barcodes that are meant to be uniform (e.g., a cellular, substrate, particle, or partition-specific barcode shared amongst all barcoded nucleic acid of a single partition, cell, or bead) can contain various N–1 deletions or other mutations from the canonical barcode sequence. Thus, barcodes that are referred to as "identical" or "substantially identical" copies refer to barcodes that differ due to one or more errors in, e.g., synthesis, polymerization, or purification errors, and thus contain various N–1 deletions or other mutations from the canonical barcode sequence. Moreover, the random conjugation of barcode nucleotides during synthesis using e.g., a split and pool approach and/or an equal mixture of nucleotide precursor molecules, can lead to low probability events in which a barcode is not absolutely unique (e.g., different from all other barcodes of a population or different from barcodes of a different partition, cell, or bead). However, such minor variations from theoretically ideal barcodes do not interfere with the high-throughput sequencing analysis methods, compositions, and kits described herein. Therefore, as used herein, the term "unique" in the context of a particle, substrate, cellular, partition-specific, or molecular barcode encompasses various inadvertent N–1 deletions and mutations from the ideal barcode sequence. In some cases, issues due to the inexact nature of barcode synthesis, polymerization, and/or amplification, are overcome by oversampling of possible barcode sequences as compared to the number of barcode sequences to be distinguished (e.g., at least about 2-, 5-, 10-fold or more possible barcode sequences). For example, 10,000 cells can be analyzed using a cellular barcode having 9 barcode nucleotides, representing 262,144 possible barcode sequences. The use of barcode technology is well known in the art, see for example Katsuyuki Shiroguchi, et al. Proc Natl Acad Sci USA., 2012 Jan. 24; 109(4):1347-52; and Smith, A M et al., Nucleic Acids Research Can 11, (2010). Further methods and compositions for using barcode technology include those described in U.S. 2016/0060621.

A "transposase" or "tagmentase" (which terms are used synonymously here) means an enzyme that is capable of forming a functional complex with a transposon end-containing composition and catalyzing insertion or transposition of the transposon end-containing composition into the double-stranded target DNA with which it is incubated in an in vitro transposition reaction. Exemplary transposases include but are not limited to modified TN5 transposases that are hyperactive compared to wildtype TN5, for example can have one or more mutations selected from E54K, M56A, or L372P or as discussed in the Background section.

"Combining the contents of droplets" refers to any way of forming a continuous mixture of the contents of multiple droplets. For example, when the droplets are present in an emulsion, the emulsion cab e broken (thereby mixing the contents of the droplets within the emulsion) by adding an agent or by application of physical force. For example, one can add a surfactant (e.g., perfluorooctanol) and/or heating. Force options include gravity and/or centrifugation.

BRIEF DESCRIPTION OF THE DRAWINGS

FIG. 1 discloses SEQ ID NOS 5-6, 5, 7, 3, and 8-10, respectively, in order of appearance.

FIG. 3 depicts 3' overhang transposase adaptor hybridization, with an extension reaction using a strand displacing polymerase in bulk. The same process as shown in FIG. 2 occurs except that a strand displacing polymerase is used to create complementary ends of the DNA in bulk.

FIG. 5 discloses SEQ ID NOS 5, 11, 3, 8, 12, 4, and 13, respectively, in order of appearance.

FIGS. 6a-c depict an exemplary method as described herein in which the adaptor oligonucleotides include a single stranded portion having a 3' part and a 5' part. The 5' part of the single-stranded portion hybridizes with the 3' end of the first oligonucleotide primer whereas the 3' part of the single-stranded portion is not complementary to the first oligonucleotide primer and so does not hybridize, thereby generating a "Y" hybridization. FIG. 6c depicts a possible sequencing reaction of the resulting DNA fragments using a sequencing primer having one or more linked nucleic acid (LNA) nucleotides.

DETAILED DESCRIPTION OF THE INVENTION

Introduction

The methods and reagents described herein provide for barcoding and analysis of DNA (e.g., purified DNA or nucleosomes) using partition (e.g., droplet) technology while avoiding performing amplification or other enzymatic reactions (e.g., ligation, DNA extension, exonuclease treatment) in droplets. For example, amplification can occur in bulk after the contents of the droplets have been merged. The inventors have determined how to obtain the benefits of partition technology, allowing for partition-specific barcoding of DNA while performing amplification (e.g., PCR) and other steps in bulk, thereby avoiding performance issues for example that can occur when PCR is performed on DNA samples that have been fragmented by a transposase.

An advantage of avoiding PCR and optionally other enzymatic steps in droplets is that one can use reagents in droplets that would otherwise be avoided due to the sensitivity of enzymes to these reagents. For example, one can use chaotropic agents (e.g., guanidine thiocyanate) or proteases in droplets. This allows for improved reactions and in some embodiments sensitivity improvements.

Transposase Reaction

Figure 1:
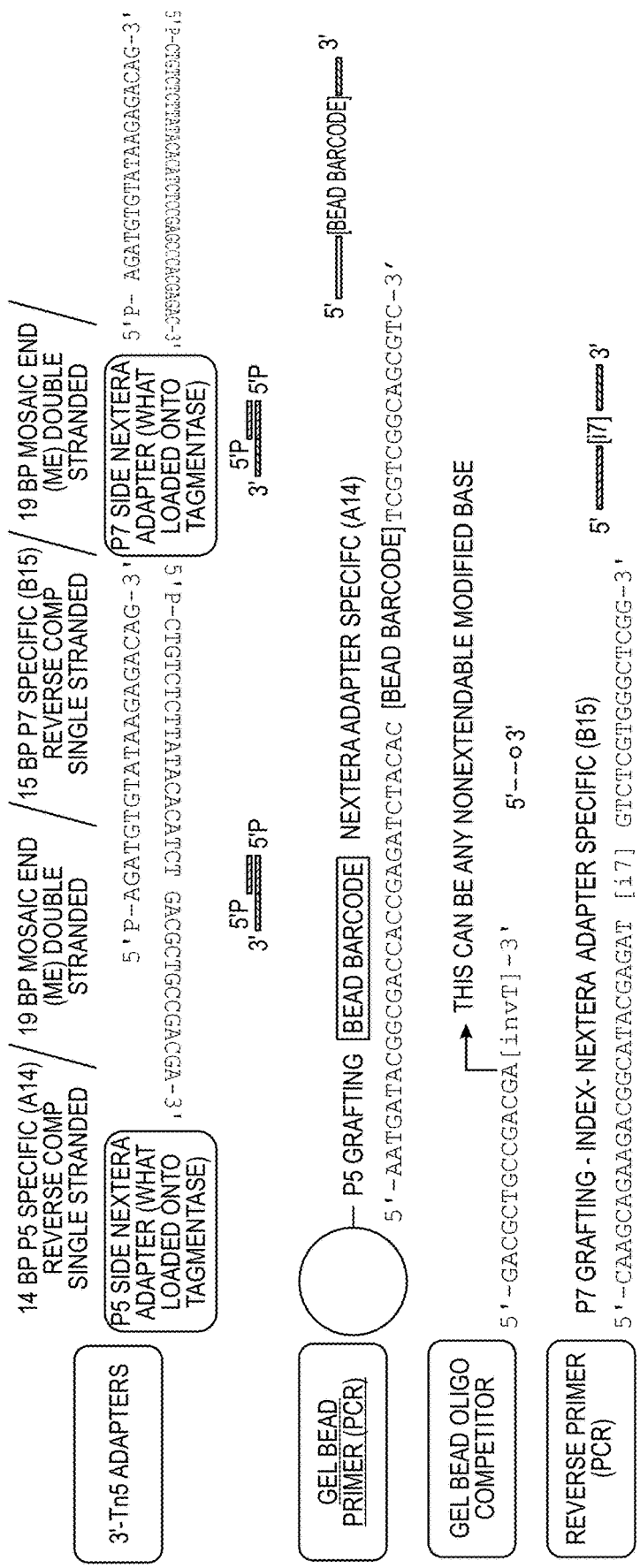
FIG. 1 depicts exemplary oligonucleotides for use in the methods described herein. The Tn5 transposase adapters contain 3' overhangs and all strands of the adapters are 5' phosphorylated. For the gel bead primer, the bead barcode can vary and can comprise a combination of fixed and variable sequences. The gel bead oligo competitor is non-extendable from the 3' end. This may be achieved by using an inverted dT as shown in the figure or by using any known non-extendable base.
Figure 2A:
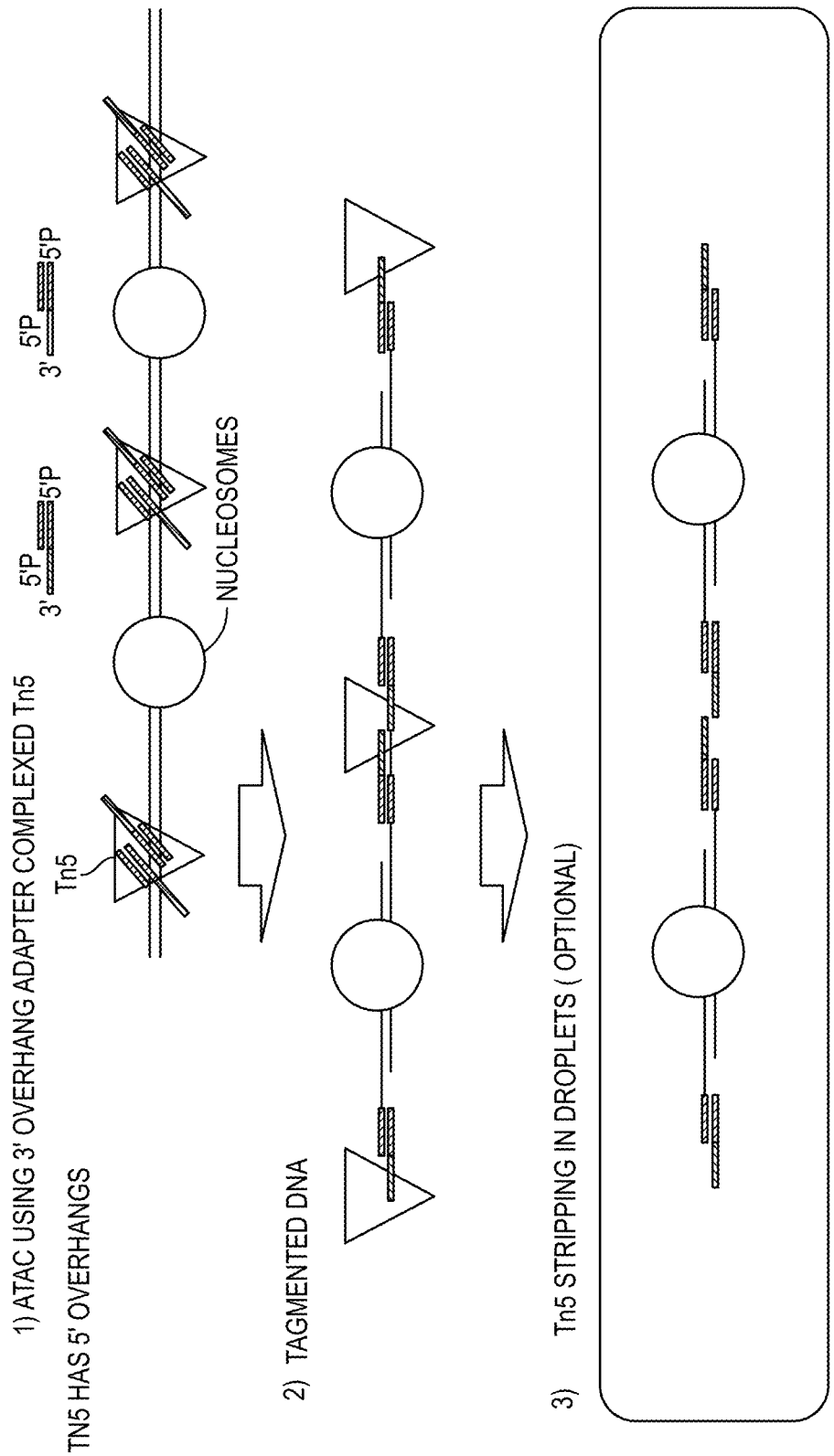
FIG. 2a-b depicts 3' overhang transposase adaptor hybridization with an extension ligation reaction in bulk. The two types of Tn5 transposase complexes used in this embodiment are shown at the top of the figure. The first step involves reacting the Tn5 complexes with DNA that is nucleosome free or free of proteins that prevent Tn5 binding. The second step involves the tagmentation of DNA, which comprises fragmentation of the double stranded substrate followed by ligation of one of the two mosaic end strands to the target DNA. The DNA with bound Tn5 is then encapsulated in droplets and the Tn5 optionally stripped. The oligonucleotide beads that had been encapsulated together with the transposed DNA in the previous step release their oligonucleotides from the beads using an agent introduced to the droplets, for example, at the moment of droplet formation. The 3' end of the bead oligonucleotides hybridize to the transposed DNA as well as the reverse PCR primer. The emulsion is broken and competitor non-extendable oligonucleotides are optionally added to the solution to prevent de novo binding of unbound oligonucleotides to unoccupied Tn5 adapters. The DNA is purified from cellular material including nucleosomes using guanidine thiocyanate and/or other protein denaturants. The DNA is then extended by its 3' end and strands are ligated at the nicks wherever 5' and 3' sequences juxtapose each other.

The methods include a step of random fragmentation of DNA by a transposase and introduction of an oligonucleotide adaptor on ends created by the fragmentation. The transposase is loaded with two oligonucleotide adapters. In some embodiments, the oligonucleotide adaptors loaded onto the transposase comprise a 3' single stranded portion (i.e., a 3' overhang) and a double stranded portion, with a first oligonucleotide having a 3' end and a 5' end and being a strand of the double-stranded portion and a second oligonucleotide comprising the single-stranded portion and a complementary strand of the double stranded portion. Exemplary single-stranded portions can be, for example, 6-30, 10-20, or 12-18 nucleotides in length. In some embodiments, the transposase is heteroadapter-loaded wherein the single-stranded portion of one of the oligonucleotide adapters is GACGCTGCCGACGA (A14; SEQ ID NO:1) and the single-stranded portion of one of the oligonucleotide adapters is CCGAGCCCACGAGAC (B15; SEQ ID NO:2). Exemplary oligonucleotide adapters are shown in the top row of FIG. 1. In some embodiments, the transposase is loaded with two different adaptor oligonucleotides having the same double stranded portion and different 3' single stranded portions. In these embodiments, the shorter strand (which forms one strand of the double-stranded region) is identical in both adaptors and it is this strand that is transferred to DNA ends. See, e.g., FIGS. 1 and 2a. However, the complement (which is the strand having single and double-stranded portions) of the transferred strand is different to the complement of the $2^{nd}$ transfer strand. The two alternatives in the first row of FIG. 1 are an exemplary set of oligonucleotide adapters that form heteroadaptors to be loaded onto the transposase. In some embodiments, one or both strand of the adaptor oligonucleotides are phosphorylated at the 5' end(s), thereby allowing for use in ligation later. Thus, contacting a target polynucleotide (e.g., genomic DNA or double-stranded cDNA) with a homoadapter-loaded transposase covalently links a single species of transferred strand to the 5' end of a fragment produced by the transposase enzyme. In some embodiments, homoadapter loaded transposases are used in a reaction mixture that does not contain a differently loaded transposase (e.g., does not contain a different homoadapter loaded transposase and does not contain a heteroadapter loaded tagmentase). In such a reaction mixture, the transferred strand is the same for every product of a tagmentation reaction.

Adapter loaded transposases are further described, e.g., in U.S. Patent Publication Nos: 2010/0120098; 2012/0301925; and 2015/0291942 and U.S. Pat. Nos. 5,965,443; 6,437,109; 7,083,980; 9,005,935; and 9,238,671, the contents of each of which are hereby incorporated by reference in the entirety for all purposes. Oligonucleotides can be loaded onto a transposase for example by initially mixing the two strands of the oligonucleotide adaptors so they are double-stranded and then contacting the double-stranded adaptor oligonucleotides to the transposase. See, e.g., U.S. Pat. No. 6,294,385.

Figure 6A:
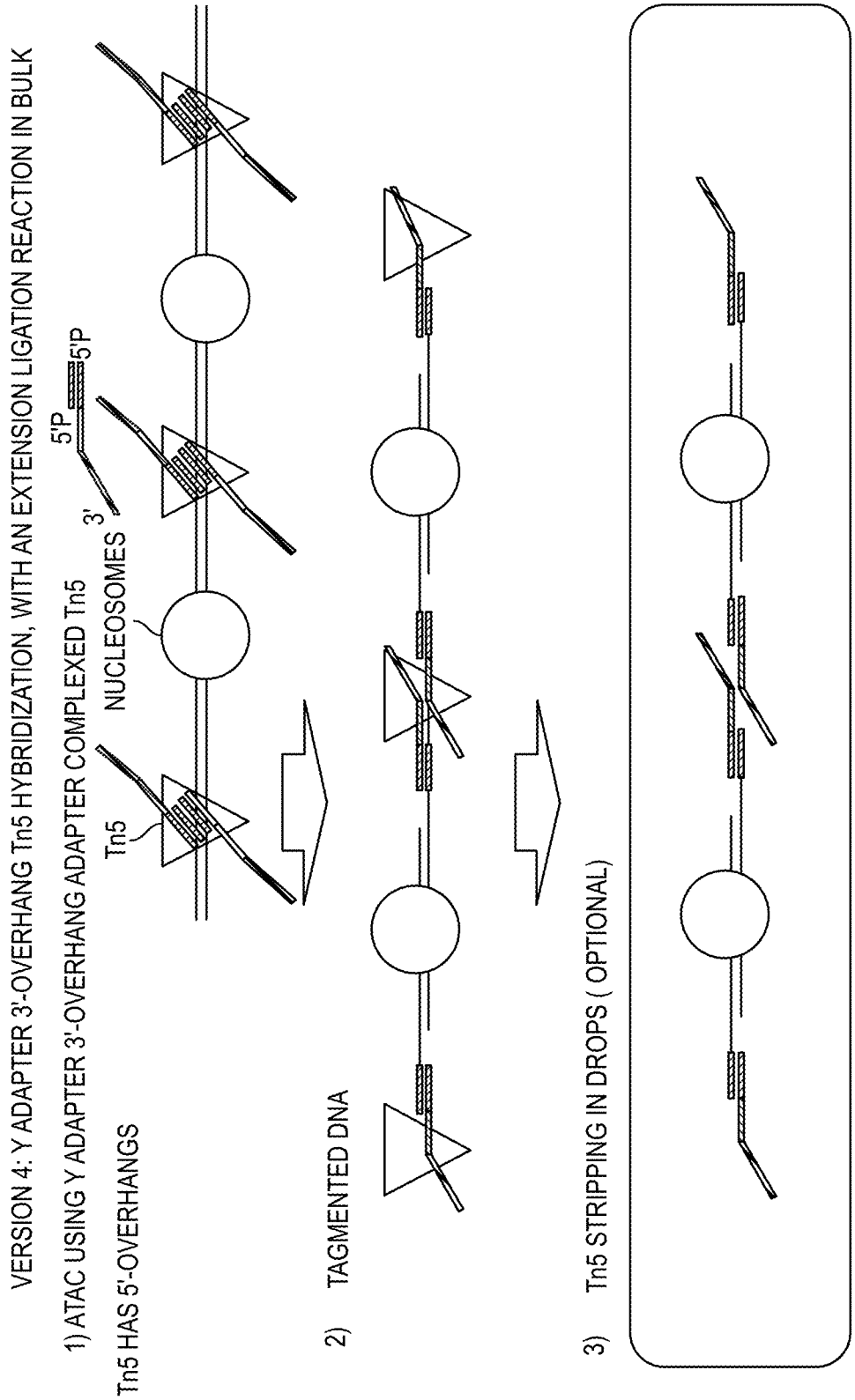

In some embodiments, the single-stranded portion of the second (adaptor) oligonucleotide comprises a 5' nucleotide sequence and a 3' nucleotide sequence (note the 3' nucleotide sequence is not at the 3' end of the oligonucleotide but is the 3' portion of the single-stranded portion). In some embodiments, the 5' nucleotide sequence is complementary to the free 3' end of the first oligonucleotide primer and the 3' nucleotide sequence of the single-stranded portion of the second (adaptor) oligonucleotide is less than 50% (e.g., less than 40%, 30%, 20%, 10%) complementary to the first oligonucleotide primer. This is depicted, for example, in FIG. 6a-b. For example in part 4 of FIG. 6b, a 5' portion of the single-stranded portion of the adaptor hybridizes to the 3' end of the first oligonucleotide primer but the 3' portion of the single stranded region of the adaptor does not hybridize to the first oligonucleotide primer (depicted in FIG. 6b as a portion at a diagonal from the "bead barcode"). This configuration improved library conversion for sequencing thus allowing for more fragments to be available for sequencing.

In some embodiments, the transposase is linked to a bead. The linkage can be covalent or non-covalent (e.g., via biotin-streptavidin or other linkage). The bead linked to the transposase in these embodiments is not the same bead as the bead described below linked to the first oligonucleotide primer. The bead linked to the transposase can be magnetic or non-magnetic. An exemplary bead for this purpose include but is not limited to Dynabeads™ M-280 Streptavidin (Thermo Fisher).

Double-stranded DNA fragmented by the transposase can be from any source as desired. For example, any genomic DNA can be used in the methods. In some embodiments, the DNA is from a single cell or is from a single type of cell from an organism. In some embodiments, the genomic DNA is from a eukaryote, for example from a mammal, e.g. a human. In some embodiments, the DNA is from a plant or fungus. In some embodiments, the starting DNA is purified as desired and used directly in the method. Alternatively, DNA can be treated to generate DNA fragments of a desired average size, for example using size-selection columns or gel purification.

Biological samples can be obtained from any biological organism, e.g., an animal, plant, fungus, pathogen (e.g., bacteria or virus), or any other organism. In some embodiments, the biological sample is from an animal, e.g., a mammal (e.g., a human or a non-human primate, a cow, horse, pig, sheep, cat, dog, mouse, or rat), a bird (e.g., chicken), or a fish. A biological sample can be any tissue or bodily fluid obtained from the biological organism, e.g., blood, a blood fraction, or a blood product (e.g., serum, plasma, platelets, red blood cells, and the like), sputum or saliva, tissue (e.g., kidney, lung, liver, heart, brain, nervous tissue, thyroid, eye, skeletal muscle, cartilage, or bone tissue); cultured cells, e.g., primary cultures, explants, and transformed cells, stem cells, stool, urine, etc. In some embodiments, the sample is a sample comprising cells. In some embodiments, the sample is a single-cell sample. In some embodiments, DNA from cells (e.g., in some aspects including cancer cells) can be shed into the blood in the form of cell-free DNA. Thus in some embodiments, the sample is DNA in such a cell-free (e.g., including but not limited to nucleosomes from cell-free DNA) sample.

In some embodiments, the transposase is applied to DNA having chromatin (e.g., histones forming nucleosomes and/or comprising other DNA accessory factors that form chromatin). In these embodiments, the transposase will not have equal access to all of the DNA because of the presence of nucleosomes. These methods are sometimes referred to as "ATAC-seq" (see, e.g., US Patent Publication No. 20160060691; Buenrostro et al. (2015) *Curr Protoc Mol Biol.* 109:21.29.1-21.29.9) and can be used to determine chromatin changes to different conditions, for example.

In other embodiments, the DNA is substantially free of protein. For example, the DNA sample has been extracted with phenol to remove DNA binding proteins.

In some embodiments the DNA is contained within its native cell. For example, the native cell can be fixed and permeabilized such that a transposase can enter the nucleus of the cell and cleave the DNA as the chromatin structure allows. This can be considered an assay for transposase accessibility of chromatin. Accordingly, in some embodiments the DNA is in the form of chromatin. In some embodiments, the DNA is a contiguity-preserved tagmented polynucleotide (e.g., DNA) sequence. In contiguity preserved transposition or tagmentation, a transposase (e.g., Tn5 transposase) is used to modify DNA with adaptor sequences while maintaining contiguity of DNA segments. Conditions for preparing contiguity preserved tagmented polynucleotide sequences are known. See, e.g., Amini et al., Nature Genetics, 2014, 46:1343-1349; WO 2016/061517; and U.S. Provisional Patent Application No. 62/436,288; each of which is incorporated by reference herein.

Once the DNA sample has been treated with the transposase, the DNA can be formed into a plurality of separate partitions, e.g., droplets. Any type of partition can be used in the methods described herein. While the method has been exemplified using droplets it should be understood that other types of partitions can also be used.

Methods and compositions for partitioning are described, for example, in published patent applications WO 2010/036,352, US 2010/0173,394, US 2011/0092,373, and US 2011/0092,376, the contents of each of which are incorporated herein by reference in the entirety. The plurality of partitions can be in a plurality of emulsion droplets, or a plurality of microwells, etc.

In some embodiments, one or more reagents are added during droplet formation or to the droplets after the droplets are formed. Methods and compositions for delivering reagents to one or more partitions include microfluidic methods as known in the art; droplet or microcapsule combining, coalescing, fusing, bursting, or degrading (e.g., as described in U.S. 2015/0027,892; US 2014/0227,684; WO 2012/149,042; and WO 2014/028,537); droplet injection methods (e.g., as described in WO 2010/151,776); and combinations thereof.

As described herein, the partitions can be picowells, nanowells, or microwells. The partitions can be pico-, nano-, or micro-reaction chambers, such as pico, nano, or microcapsules. The partitions can be pico-, nano-, or microchannels. The partitions can be droplets, e.g., emulsion droplets.

In some embodiments, the partitions are droplets. In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated from a sample coalesce with other droplets. The emulsions can also have limited flocculation, a process by which the dispersed phase comes out of suspension in flakes. In some cases, such stability or minimal coalescence is maintained for up to 4, 6, 8, 10, 12, 24, or 48 hours or more (e.g., at room temperature, or at about 0, 2, 4, 6, 8, 10, or 12° C.). In some embodiments, the droplet is formed by flowing an oil phase through an aqueous sample or reagents.

The oil phase can comprise a fluorinated base oil which can additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H, 2H,2H-Perfluorodecanol is added to a concentration of about 0.18% (w/w).

In some embodiments, the emulsion is formulated to produce highly monodisperse droplets having a liquid-like interfacial film that can be converted by heating into microcapsules having a solid-like interfacial film; such microcapsules can behave as bioreactors able to retain their contents through an incubation period. The conversion to microcapsule form can occur upon heating. For example, such conversion can occur at a temperature of greater than about 40°, 50°, 60°, 70°, 80°, 90°, or 95° C. During the heating process, a fluid or mineral oil overlay can be used to prevent evaporation. Excess continuous phase oil can be removed prior to heating, or left in place. The microcapsules can be resistant to coalescence and/or flocculation across a wide range of thermal and mechanical processing.

Following conversion of droplets into microcapsules, the microcapsules can be stored at about −70°, 20°, 0°, 3°, 4°, 5°, 6°, 7°, 8°, 9°, 10°, 15°, 20°, 25°, 30°, 35° or 40° C. In some embodiments, these capsules are useful for storage or transport of partition mixtures. For example, samples can be collected at one location, partitioned into droplets containing enzymes, buffers, and/or primers or other probes, optionally one or more polymerization reactions can be performed, the partitions can then be heated to perform microencapsulation, and the microcapsules can be stored or transported for further analysis.

In some embodiments, the sample is partitioned into, or into at least, 500 partitions, 1000 partitions, 2000 partitions, 3000 partitions, 4000 partitions, 5000 partitions, 6000 partitions, 7000 partitions, 8000 partitions, 10,000 partitions, 15,000 partitions, 20,000 partitions, 30,000 partitions, 40,000 partitions, 50,000 partitions, 60,000 partitions, 70,000 partitions, 80,000 partitions, 90,000 partitions, 100,000 partitions, 200,000 partitions, 300,000 partitions, 400,000 partitions, 500,000 partitions, 600,000 partitions, 700,000 partitions, 800,000 partitions, 900,000 partitions, 1,000,000 partitions, 2,000,000 partitions, 3,000,000 partitions, 4,000,000 partitions, 5,000,000 partitions, 10,000,000 partitions, 20,000,000 partitions, 30,000,000 partitions, 40,000,000 partitions, 50,000,000 partitions, 60,000,000 partitions, 70,000,000 partitions, 80,000,000 partitions, 90,000,000 partitions, 100,000,000 partitions, 150,000,000 partitions, or 200,000,000 partitions.

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, the standard deviation of droplet volume can be less than about 1 picoliter, 5 picoliters, 10 picoliters, 100 picoliters, 1 nL, or less than about 10 nL. In some cases, the standard deviation of droplet volume can be less than about 10-25% of the average droplet volume. In some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

In some embodiments, formation of the droplets results in droplets that comprise the DNA that has been previously treated with the transposase and a first oligonucleotide primer linked to a bead. The term "bead" refers to any solid support that can be in a partition, e.g., a small particle or other solid support. Exemplary beads can include hydrogel beads. In some cases, the hydrogel is in sol form. In some cases, the hydrogel is in gel form. An exemplary hydrogel is an agarose hydrogel. Other hydrogels include, but are not limited to, those described in, e.g., U.S. Pat. Nos. 4,438,258; 6,534,083; 8,008,476; 8,329,763; U.S. Patent Appl. Nos. 2002/0,009,591; 2013/0,022,569; 2013/0,034,592; and International Patent Publication Nos. WO/1997/030092; and WO/2001/049240.

Methods of linking oligonucleotides to beads are described in, e.g., WO 2015/200541. In some embodiments, the oligonucleotide configured to link the hydrogel to the barcode is covalently linked to the hydrogel. Numerous methods for covalently linking an oligonucleotide to one or more hydrogel matrices are known in the art. As but one example, aldehyde derivatized agarose can be covalently linked to a 5'-amine group of a synthetic oligonucleotide.

As noted above, the partitions will include one or a few (e.g., 1, 2, 3, 4) beads per partition, where in each bead is linked to a first oligonucleotide primer having a free 3' end. The first oligonucleotide primer will have a bead-specific barcode and a 3' end that is complementary to an adaptor. In some embodiments, the barcode will be, e.g., 2-10 nucleotides in length, e.g., 2, 3, 4, 5, 6, 7, 8, 9, or 10 nucleotides. The barcode can be continuous or discontinuous, i.e., broken up by other nucleotides. In some embodiments, the 3' end will be at least 50% complementary (e.g., at least 60%, 70%, 80%, 90% or 100%) complementary (such that they hybridize) to the entire adaptor sequence. In some embodiments, at least the 3'-most 6, 7, 8, 9, 10, 11, 12, 13, 14, 15, 16, 17, 18, 19, or 20 of the oligonucleotide are at least 50% complementary (e.g., at least 60%, 70%, 80%, 90% or 100%) complementary to a sequence in the adaptor. The adaptor sequence in some embodiments comprises GACGCTGCCGACGA (A14; SEQ ID NO:1) or CCGAGCCCACGAGAC (B15; SEQ ID NO:2). In some embodiments, the first oligonucleotide primer further comprises a universal or other additional sequence to assist with downstream manipulation or sequencing of the amplicon. For example, when Illumina-based sequencing is used the first oligonucleotide primer can have a 5' P5 or P7 sequence (optionally with the second oligonucleotide primer having the other of the two sequences). Optionally, the first oligonucleotide primer comprises a restriction or cleavage site to remove the first oligonucleotide primer from the bead when desired. In some cases, the first oligonucleotide primer is attached to a solid support (e.g., bead) through a disulfide linkage (e.g., through a disulfide bond between a sulfide of the solid support and a sulfide covalently attached to the 5' or 3' end, or an intervening nucleic acid, of the oligonucleotide). In such cases, the oligonucleotide can be cleaved from the solid support by contacting the solid support with a reducing agent such as a thiol or phosphine reagent, including but not limited to a beta mercaptoethanol, dithiothreitol (DTT), or tris(2-carboxyethyl)phosphine (TCEP). In some embodiments, once the DNA segments are in the partitions with the bead-linked first oligonucleotide primer but prior to hybridization, the first oligonucleotide primer is cleaved from the bead prior to amplification. To the extent more than one bead (and thus bead-specific barcode via the first oligonucleotide primer) is introduced into a droplet, deconvolution can be used to orient sequence data from a particular bead to that bead. One approach for deconvoluting which beads are present together in a single partition is to provide partitions with substrates comprising barcode sequences for generating a unique combination of sequences for beads in a particular partition, such that upon their sequence analysis (e.g., by next-generation sequencing), the beads are virtually linked. See, e.g., PCT Application WO2017/120531.

Figure 2B:
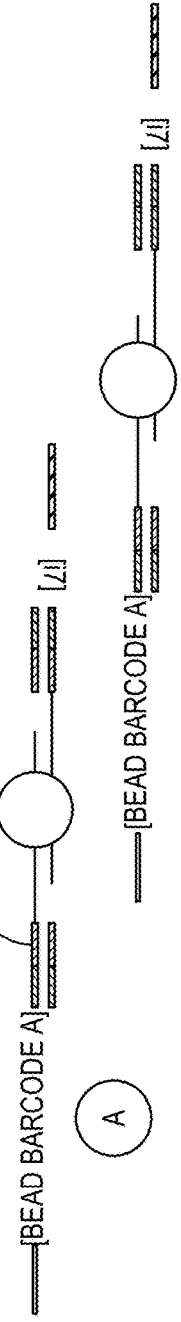

As noted above, in some embodiments, the partitions further include a second oligonucleotide primer that functions as a reverse primer in combination with the first oligonucleotide primer. See, e.g., FIGS. 1 and 2b. The 3' end of the second oligonucleotide primer is at least 50% complementary (e.g., at least 60%, 70%, 80%, 90% or 100%) complementary to a 3' single-stranded portion of an oligonucleotide adaptor ligated to a DNA fragment. See, e.g., FIG. 2b. In some embodiments, the 3' end of the second oligonucleotide primer will be complementary to the entire adaptor sequence. In some embodiments, at least the 3'-most 6, 7, 8, 9, 10, 11, 12, 13, 14, 15, 16, 17, 18, 19, or 20 of the second oligonucleotide primer are complementary to a sequence in the adaptor. In some embodiments, the second oligonucleotide primer comprises a barcode sequence, which for example can be of the same length as listed above for the barcode of the first oligonucleotide primer. In some embodiments, the barcode includes an index barcode, e.g., a sample barcode, e.g., Illumina i7 or i5 sequences.

The amount and type of DNA within a partition can vary as desired. For example, in some embodiments, all of the DNA from the sample that is in a particular partition is from a single cell or nuclei. In some embodiments, the DNA in a droplet is no more than 0.02% haploid genomes. In some embodiments, the partitions contain 60 megabases or less of DNA. When each of the partitions contain less DNA, more partitions are required to achieve the same resolution of data. In some embodiments the partitions have on average 1 kb-10 Megabases of DNA.

In some embodiments, where information about a haploid genome is desired, the DNA in the droplets is maintained such that contiguity between fragments created by the transposase is maintained. This can be achieved for example, by selecting conditions such that the transposase does not release from the DNA, and thus forms a bridge linking DNA segments that have the same relationship (haplotype) as occurred in the genomic DNA. For example, transposase has been observed to remain bound to DNA until a detergent such as SDS is added to the reaction (Amini et al. *Nature Genetics* 46(12): 1343-1349).

Optionally, in some embodiments, the transposase is stripped from the DNA following droplet formation, i.e., within the partitions/droplets. In embodiments in which enzymatic reactions do not occur in droplets, one can employ more harsh reagents in the droplets. This can improve reactions where the reagents are employed and such reagents can be removed prior to subsequent enzymatic reactions that occur in bulk. For example, DNA/transposase complexes can be combined with an agent that removes the transposase from the DNA. In some embodiments, the agent is a detergent, e.g., an ionic or non-ionic detergent. An exemplary detergent is sodium dodecyl sulfate (SDS). In some embodiments, concentrations of 0.1 and 0.2% SDS are sufficient to remove the tagmentase and yet are sufficiently low to not interfere with amplification. In some embodiments, the transposase is digested, e.g., by protease digestion, e.g., proteinase K digestion. In some embodiments, the transposase is stripped from the DNA by contact with a chaotrope, e.g., guanidine thiocyanate. In some embodiments (e.g., in which droplets are used) the agent is compatible with droplet formation.

The partitions (e.g., droplets) formed above can in some embodiments further include a second oligonucleotide primer. See, for example, FIG. 2b. In some embodiments, the second oligonucleotide primer is not linked to a bead or other solid support. In some embodiments, the second oligonucleotide primer acts as a second part of a pair of amplification primers with the first oligonucleotide primer. In some embodiments, for example, the second oligonucleotide primer acts as a reverse primer. For example, the second oligonucleotide primer can have a 3' end complementary to one of the single-stranded portion of the oligonucleotide adaptors, wherein the first oligonucleotide primer 3' end and the second oligonucleotide primer 3' end are complementary to single-stranded portions of different oligonucleotide adaptors. In some embodiments, the second oligonucleotide primer will include a 5' PCR handle sequence (e.g., P5 or P7 sequence (optionally with the first oligonucleotide primer having the other of the two sequences)). The PCR handle can be, for example, between 2-40 nucleotides, e.g., 10-30 nucleotides in length.

Thus in some embodiments, the partitions comprise the fragmented and transposase-treated DNA, and the first oligonucleotide primer and the second oligonucleotide primers, which two primers act as forward and reverse primers for the fragments having different adaptors on either end. See, for example, FIG. 2b. As the first oligonucleotide will include a bead-based (or partition)-specific barcode, and different partitions will in general have one or very few first oligonucleotide primer beads, each with unique bead-specific barcodes, each partition (e.g., droplet) can subsequently be used to barcode DNA fragments with a partition (e.g., bead-)-specific barcode. In embodiments in which contiguity was preserved, for example, haploid genomes will thus include the same bead-specific barcode. In embodiments where the DNA is in chromatin and contained within the nuclei, the cell's ATAC DNA (DNA in the form of chromatin that is accessible to the transposase) will thus also include the same bead-specific barcode.

Accordingly, following formation of the partitions containing at least one, and in some embodiments the first and second oligonucleotide primer, these primers are hybridized to the adaptor sequences at the end of the DNA fragments. Hybridization conditions can be selected as desired to allow for specific hybridization of the primers to the adaptors.

Once hybridization has occurred, but before enzymatic reactions, the contents of the various (e.g., 100s, 1000s, or many more) partitions can be merged. Any method of combining droplets can be used. Exemplary methods of combining droplets can be found in, e.g., Priest et al. (2006) Appl. Phys. Lett., 89: 134101:1-134101:3; Ahn et al. (2006) Appl. Phys. Lett., 88: 264105; Fidalgo et al. (2007) Lab Chip, 7(8): 984-986; Tan et al. (2004) Lab Chip, 4(4): 292-298.

In some embodiments, histones, non-DNA nucleosomal factors, and/or chromatin can be removed in the droplet. For example, once droplets have formed, the resulting mixture can be contacted by an agent to remove these items. In some embodiments, the droplets are formed by merging two aqueous streams (e.g., in combination with an immiscible liquid) with the agent originating from one of the aqueous streams used to create a droplet with the other stream containing the DNA substrate. Agents for removal of these items from the DNA can include, for example, protease digestion, e.g., proteinase K digestion or contact with a chaotrope, e.g., guanidine thiocyanate. This can help to maximize the number of binding sites to the first oligonucleotide primers that are released from the beads.

Optionally, once droplets have been merged, the resulting bulk mixture can be contacted with an agent to remove histones. An exemplary agent is for example, guanidine thiocyanate.

Optionally, before, during or after combining, competitor oligonucleotides can be introduced into the mixture to hybridize to unbound copies of reagents, thereby reducing the misattribution of barcodes to multiple droplets. For example, in some embodiments, a competitor oligonucleotide can be introduced in sufficient concentration such that it, or a single-stranded portion thereof, hybridizes to 3' ends of unbound copies of the first oligonucleotide primer, thereby preventing de novo binding of unbound DNA fragments after the combining. In some embodiments, a competitor oligonucleotide can be introduced in sufficient concentration such that it, or a single-stranded portion thereof, hybridizes to 3' ends of unbound copies of the oligonucleotide adaptors, thereby preventing de novo binding of unbound DNA fragments after the combining. The competitor oligonucleotides can for example be at least 10 nucleotides in length and in some embodiments not longer than the primer binding portion of the first oligonucleotide primer. In some embodiments, the competitor oligonucleotides comprise the reverse compliment of A14 GACGCTGCCGACGA (SEQ ID NO: 1) or B15 CCGAGCCCACGAGAC (SEQ ID NO: 2), or different competitor oligonucleotides are used that each have a separate one of these sequences. In some embodiments, the competitor oligonucleotide concentration is at least 2× more than the final concentration of the first oligonucleotide primer. In some embodiments the competitor oligonucleotide concentration is between 200 nM and 10 µM.

Once the contents of the droplets have been combined, the DNA is contacted with one or more enzyme to manipulate the DNA. For examine, in some embodiments, the DNA fragments hybridized to the oligonucleotide primers as described herein, can be contacted with a ligase, a polymerase, or both, thereby ligating the first oligonucleotide primer 3' end to the 5' end of an oligonucleotide adaptor at the end of a DNA fragment.

Figure 4:
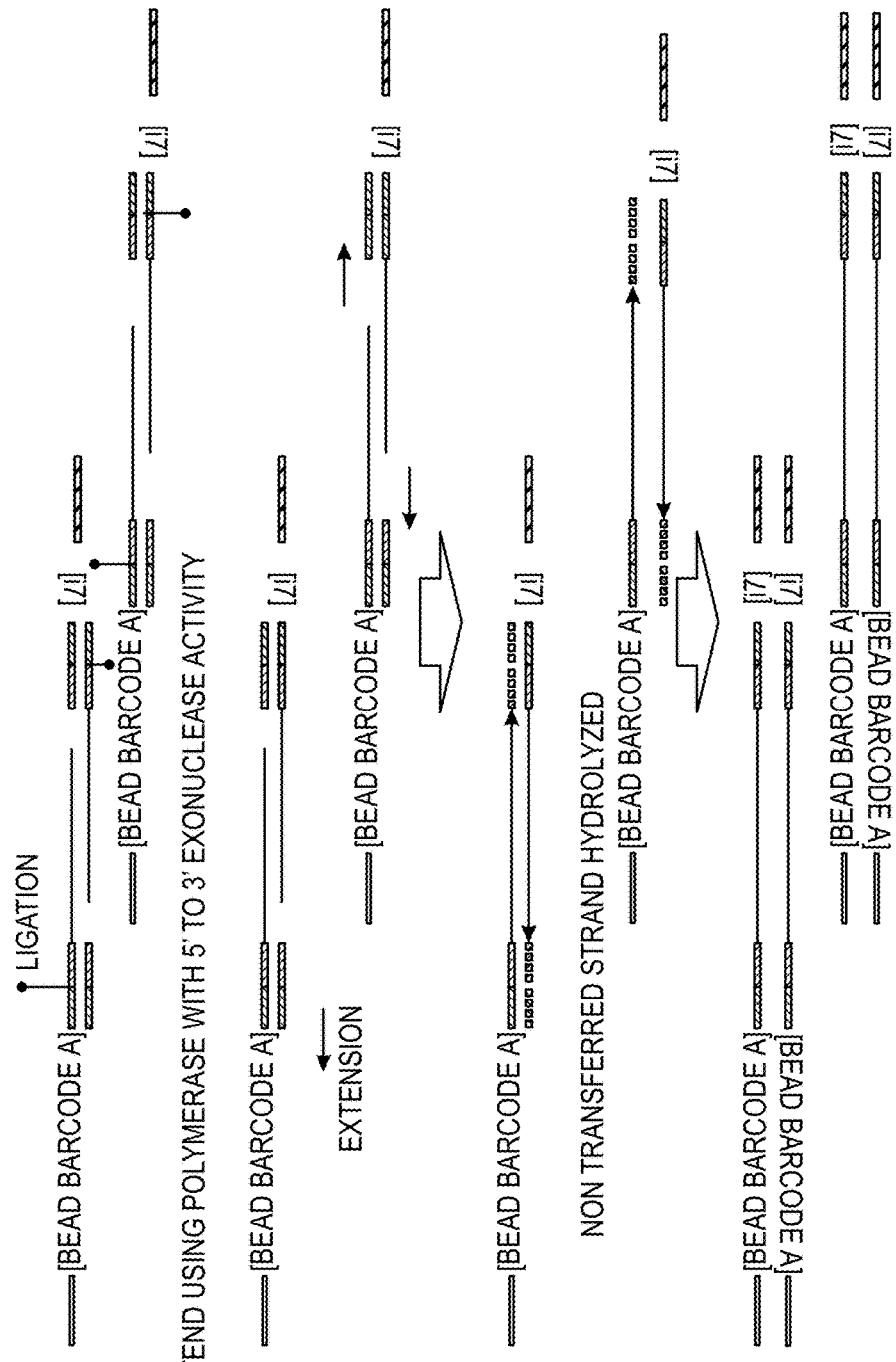
FIG. 4 depicts 3' overhang transposase adaptor hybridization, with an extension reaction only using a polymerase with 5' to 3' exonuclease activity in bulk. The same process as shown in FIG. 2 occurs except that a DNA polymerase with 5' to 3' exonuclease activity is used to create complementary ends of the DNA in bulk.
Figure 5:
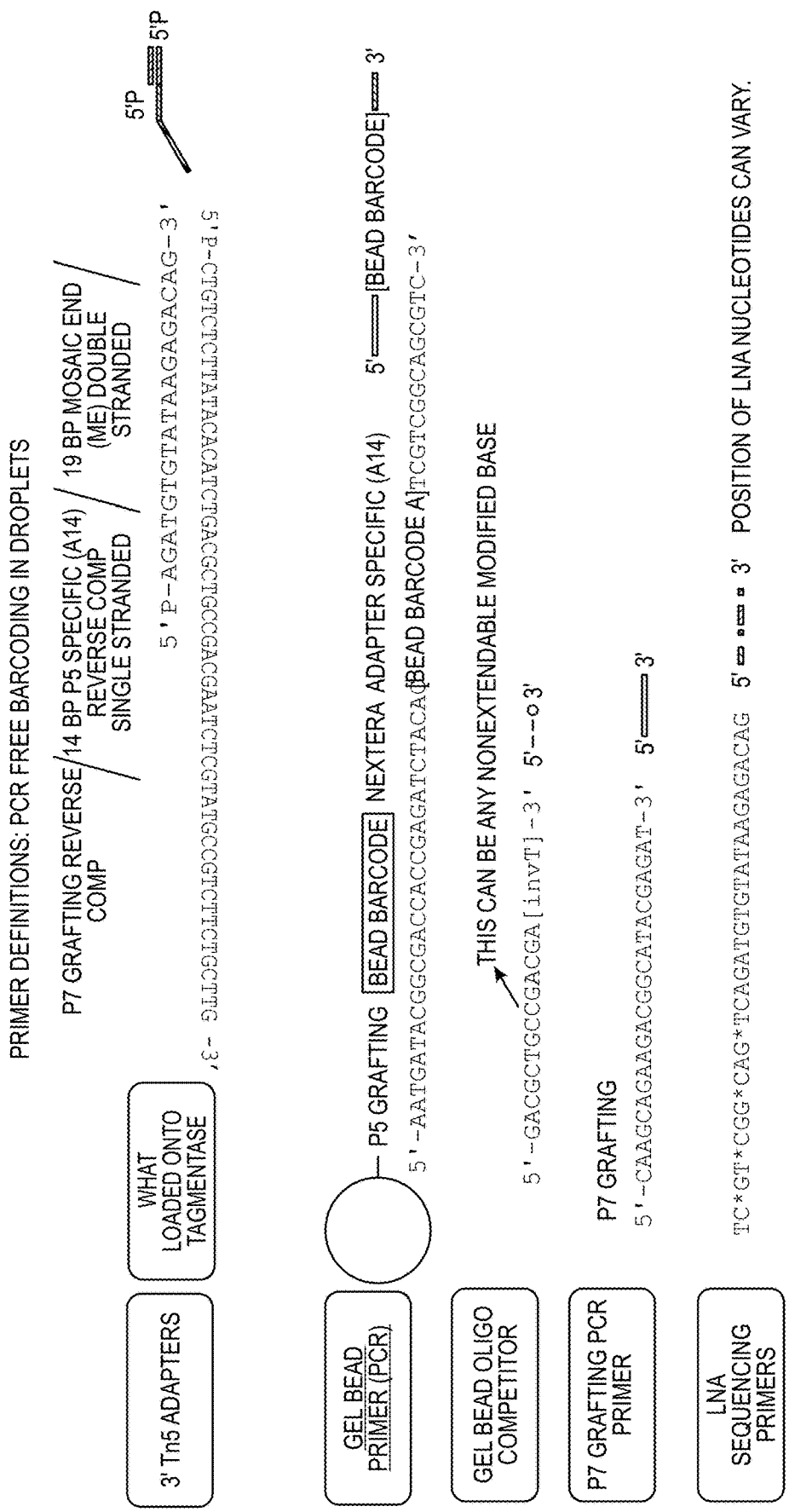
FIG. 5 depicts exemplary oligonucleotides for use in the methods described herein. The Tn5 adapters contain 3' overhangs that comprise the full P7 sequence, Tn5 A14 and mosaic end (ME) sequences. All strands of the adapters are 5' phosphorylated. For the gel bead primer, the bead barcode can vary and can comprise a combination of fixed and variable sequences. The gel bead oligonucleotide competitor is non-extendable from the 3' end. This may be achieved by using an inverted dT as shown in the figure or by using a non-extendable base. The P7 and P5 grafting sequences are shown as well as an example of an LNA sequencing primer.

In some embodiments, following hybridization, the 3' end of the first oligonucleotide primer (and if present, the 3' end of the second oligonucleotide primer) can be ligated to the adaptors on the DNA fragments. Optionally, in combination (before, after, or simultaneously) with ligation, 5' overhangs can be filled ("gap filled") by a polymerase to create a double-stranded sequence by extending 3' ends. See, e.g., FIG. 2b. Following gap filling, additional ligations can be performed. In some embodiments, the polymerase can either have strand displacing activity (see, FIG. 3) or 5' to 3' exo activity (see, FIG. 4).

If desired, the resulting DNA products can be amplified, for example using forward and reverse primers that hybridize to the PCR handle sequences on the first and second oligonucleotide primers. Any type of amplification can be used, including but not limited to PCR.

In embodiments in which complementary sequences occur on either end of the amplicon the complementary sequences can form hairpins when the DNA is rendered single stranded. To avoid formation of hairpins, sequencing primers can be used that contain one or more artificial nucleotide that form higher affinity base pairing (e.g., higher Tm) than occurs in natural nucleotides thereby favoring hybridization of the sequencing primer compared to the hairpin. Exemplary artificial nucleotides can include but are not limited to Locked Nucleic Acid (LNA™).

Any method of nucleotide sequencing can be used as desired so long as at least some of the DNA segments sequence and the barcode sequence is determined. Methods for high throughput sequencing and genotyping are known in the art. For example, such sequencing technologies include, but are not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety.

Exemplary DNA sequencing techniques include fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the present technology provides parallel sequencing of partitioned amplicons (PCT Publication No. WO 2006/0841,32, herein incorporated by reference in its entirety). In some embodiments, DNA sequencing is achieved by parallel oligonucleotide extension (See, e.g., U.S. Pat. Nos. 5,750,341; and 6,306,597, both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; and U.S. Pat. Nos. 6,432,360; 6,485,944; 6,511, 803; herein incorporated by reference in their entireties), the 454 picotiter pyrosequencing technology (Margulies et al., 2005 Nature 437, 376-380; U.S. Publication No. 2005/0130173; herein incorporated by reference in their entireties), the Solexa single base addition technology (Bennett et al., 2005, Pharmacogenomics, 6, 373-382; U.S. Pat. Nos. 6,787,308; and 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 2000/018957; herein incorporated by reference in its entirety).

Typically, high throughput sequencing methods share the common feature of massively parallel, high-throughput strategies, with the goal of lower costs in comparison to older sequencing methods (See, e.g., Voelkerding et al., Clinical Chem., 55: 641-658, 2009; MacLean et al., Nature Rev. Microbiol., 7:287-296; each herein incorporated by reference in their entirety). Such methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and platforms commercialized by VisiGen, Oxford Nanopore Technologies Ltd., Life Technologies/Ion Torrent, and Pacific Biosciences, respectively.

In pyrosequencing (Voelkerding et al., Clinical Chem., 55: 641-658, 2009; MacLean et al., Nature Rev. Microbial., 7:287-296; U.S. Pat. Nos. 6,210,891; and 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., Clinical Chem., 55. 641-658, 2009; MacLean et al., Nature Rev. Microbial., 7:287-296; U.S. Pat. Nos. 6,833,246; 7,115,400; and 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbial., 7:287-296; U.S. Pat. Nos. 5,912,148; and 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing is employed (See, e.g., Astier et al., J. Am. Chem. Soc. 2006 Feb. 8; 128(5)1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, HeliScope by Helicos BioSciences is employed (Voelkerding et al., Clinical Chem., 55. 641-658, 2009; MacLean et al., Nature Rev. Microbial, 7:287-296; U.S. Pat. Nos. 7,169,560; 7,282,337; 7,482,120; 7,501,245; 6,818,395; 6,911,345; and 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (See, e.g., Science 327 (5970): 1190 (2010); U.S. Pat. Appl. Pub. Nos. 2009/0026082; 2009/0127589; 2010/0301398; 2010/0197507; 2010/0188073; and 2010/0137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers the hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

Another exemplary nucleic acid sequencing approach that may be adapted for use with the present invention was developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 2009/0035777, which is incorporated herein in its entirety.

Other single molecule sequencing methods include real-time sequencing by synthesis using a VisiGen platform (Voelkerding et al., Clinical Chem., 55: 641-58, 2009; U.S. Pat. No. 7,329,492; and U.S. patent application Ser. Nos. 11/671,956; and 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

Another real-time single molecule sequencing system developed by Pacific Biosciences (Voelkerding et al., Clinical Chem., 55. 641-658, 2009; MacLean et al., Nature Rev. Microbiol., 7:287-296; U.S. Pat. Nos. 7,170,050; 7,302,146; 7,313,308; and 7,476,503; all of which are herein incorporated by reference) utilizes reaction wells 50-100 nm in diameter and encompassing a reaction volume of approximately 20 zeptoliters ($10^{-21}$ L). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In certain embodiments, the single molecule real time (SMRT) DNA sequencing methods using zero-mode waveguides (ZMWs) developed by Pacific Biosciences, or similar methods, are employed. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters ($10^{-21}$ L). At this volume, the activity of a single molecule can be detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Phospholinked nucleotides, each type labeled with a different colored fluorophore, are then introduced into the reaction solution at high concentrations which promote enzyme speed, accuracy, and processivity. Due to the small size of the ZMW, even at these high concentrations, the detection volume is occupied by nucleotides only a small fraction of the time. In addition, visits to the detection volume are fast, lasting only a few microseconds, due to the very small distance that diffusion has to carry the nucleotides. The result is a very low background.

Processes and systems for such real time sequencing that may be adapted for use with the methods described herein are described in, for example, U.S. Pat. Nos. 7,405,281; 7,315,019; 7,313,308; 7,302,146; and 7,170,050; and U.S. Pat. Pub. Nos. 2008/0212960; 2008/0206764; 2008/0199932; 2008/0199874; 2008/0176769; 2008/0176316; 2008/0176241; 2008/0165346; 2008/0160531; 2008/0157005; 2008/0153100; 2008/0153095; 2008/0152281; 2008/0152280; 2008/0145278; 2008/0128627; 2008/0108082; 2008/0095488; 2008/0080059; 2008/0050747; 2008/0032301; 2008/0030628; 2008/0009007; 2007/0238679; 2007/0231804; 2007/0206187; 2007/0196846; 2007/0188750; 2007/0161017; 2007/0141598; 2007/0134128; 2007/0128133; 2007/0077564; 2007/0072196; and 2007/0036511; and Korlach et al. (2008) "Selective aluminum passivation for targeted immobilization of single DNA polymerase molecules in zero-mode waveguide nanostructures" PNAS 105(4): 1176-81, all of which are herein incorporated by reference in their entireties.

Upon completion of sequencing, sequences can be sorted by same barcode, wherein sequences having the same barcode came from the same partition and thus are contiguous. In some embodiments, sequences linked based on common barcode sequence can be determined and optionally SNPs can be detected per fragment per barcode. In some embodiments, one can detect fragment colocalization to a single barcode greater than chance (skewed distributions), thereby detecting a rearrangement.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. A method of barcoding DNA, the method comprising introducing oligonucleotide adaptors randomly into DNA by contacting the DNA with a transposase loaded with the oligonucleotide adaptors,
wherein the oligonucleotide adaptors comprise a single stranded portion and a double stranded portion, and
wherein the transposase introduces double-stranded breaks into the DNA, wherein each double-stranded break forms two DNA ends and the transposase ligates the oligonucleotide adaptors to one strand of each DNA end, to form DNA fragments comprising the oligonucleotide adaptors at both ends;
forming partitions, wherein the partitions contain the DNA fragments and a first oligonucleotide primer having a bead-specific barcode sequence, wherein the first oligonucleotide primer is linked to a bead and comprises a free 3' end;
in the partitions, gap filling 5' overhangs with a polymerase that has strand displacing activity or 5' to 3' exonuclease activity to create a double-stranded sequence by extending 3' ends;
hybridizing the 3' end of the first oligonucleotide primer to a 3' end of the oligonucleotide adaptor; and
combining contents of the partitions to form a reaction mixture, further comprising during the combining, mixing the contents of the partitions with a competitor oligonucleotide comprising the single-stranded portion, which (i) hybridizes to 3' ends of unbound copies of the first oligonucleotide primer or (ii) hybridizes to unbound copies of the oligonucleotide adaptors, thereby preventing de novo binding of unbound DNA fragments after the combining;
thereby generating barcoded DNA fragments.

2. The method of claim 1, further comprising amplifying the barcoded fragments.

3. The method of claim 2, wherein the amplifying comprises polymerase chain reaction.

4. The method of claim 1, comprising cleaving the oligonucleotide primer from beads before the hybridizing.

5. The method of claim 1, wherein the transposase is loaded with two different adaptor oligonucleotides having the same double stranded portion and different single stranded portions.

6. The method of claim 1, wherein the transposase is loaded with two identical adaptor oligonucleotides.

7. The method of claim 1, wherein the DNA comprises DNA-bound proteins during the introducing and the method further comprises removing the DNA-bound proteins from the DNA before the combining.

8. The method of claim 1, wherein the forming maintains contiguity of the DNA fragments compared to the DNA.

9. The method of claim 1, wherein the competitor oligonucleotide comprising the single-stranded portion hybridizes to 3' ends of unbound copies of the first oligonucleotide primer.

10. The method of claim 1, wherein the competitor oligonucleotide comprising the single-stranded portion hybridizes to 3' ends of unbound copies of the oligonucleotide adaptors.

11. The method of claim 10, wherein the competitor oligonucleotides comprise 3' ends that are not extendable by a polymerase.

12. The method of claim 7, wherein the removing comprises contacting the DNA with a chaotropic agent or protease.

13. The method of claim 1, wherein the polymerase in the contacting is a strand displacement polymerase.

14. The method of claim 1, wherein the polymerase in the contacting has 5'-3' exonuclease activity.

15. The method of claim 1, wherein the transposase is a TN5 transposase.

16. The method of claim 1, wherein the transposase is linked to a solid support.

17. The method of claim 1, further comprising sequencing the barcoded DNA sequences, wherein the sequencing comprises hybridizing and extending a sequencing primer to the barcoded DNA sequences.

18. The method of claim 1, wherein the partitions are picowells, nanowells, or microwells.

19. The method of claim 1, wherein the partitions are pico-reaction chambers, nano-reaction chambers, or micro-reaction chambers.

20. The method of claim 1, wherein the partitions are pico-channels, nano-channels, or micro-channels.

* * * * *

```
                               SEQUENCE LISTING

<160> NUMBER OF SEQ ID NOS: 13

<210> SEQ ID NO 1
  <211> LENGTH: 14
  <212> TYPE: DNA
  <213> ORGANISM: Artificial Sequence
  <220> FEATURE:
  <223> OTHER INFORMATION: Description of Artificial Sequence: Synthetic
        oligonucleotide

<400> SEQUENCE: 1
gacgctgccg acga                                                         14

<210> SEQ ID NO 2
  <211> LENGTH: 15
  <212> TYPE: DNA
  <213> ORGANISM: Artificial Sequence
  <220> FEATURE:
  <223> OTHER INFORMATION: Description of Artificial Sequence: Synthetic
        oligonucleotide

<400> SEQUENCE: 2
ccgagcccac gagac                                                        15

<210> SEQ ID NO 3
  <211> LENGTH: 29
  <212> TYPE: DNA
  <213> ORGANISM: Artificial Sequence
  <220> FEATURE:
  <223> OTHER INFORMATION: Description of Artificial Sequence: Synthetic
        primer

<400> SEQUENCE: 3
aatgatacgg cgaccaccga gatctacac                                         29

<210> SEQ ID NO 4
  <211> LENGTH: 24
  <212> TYPE: DNA
  <213> ORGANISM: Artificial Sequence
  <220> FEATURE:
  <223> OTHER INFORMATION: Description of Artificial Sequence: Synthetic
        primer

<400> SEQUENCE: 4
caagcagaag acggcatacg agat                                              24

<210> SEQ ID NO 5
  <211> LENGTH: 19
  <212> TYPE: DNA
  <213> ORGANISM: Artificial Sequence
  <220> FEATURE:
  <223> OTHER INFORMATION: Description of Artificial Sequence: Synthetic
        oligonucleotide

<400> SEQUENCE: 5
agatgtgtat aagagacag                                                    19

<210> SEQ ID NO 6
  <211> LENGTH: 33
  <212> TYPE: DNA
  <213> ORGANISM: Artificial Sequence
  <220> FEATURE:
  <223> OTHER INFORMATION: Description of Artificial Sequence: Synthetic
``` oligonucleotide

<400> SEQUENCE: 6
ctgtctctta tacacatctg acgctgccga cga                                      33

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctgtctctta tacacatctc cgagcccacg agac                                     34

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcgtcggcag cgtc                                                           14

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gacgctgccg acgat                                                          15

<210> SEQ ID NO 10
<211> LENGTH: 47
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(32)
<223> OTHER INFORMATION: a, c, t, g, unknown or other

<400> SEQUENCE: 10
caagcagaag acggcatacg agatnnnnnn nngtctcgtg ggctcgg                       47

<210> SEQ ID NO 11
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctgtctctta tacacatctg acgctgccga cgaatctcgt atgccgtctt ctgcttg            57

<210> SEQ ID NO 12
<211> LENGTH: 15
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 12
gacgctgccg acgat                                                      15

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tcgtcggcag cgtcagatgt gtataagaga cag                                  33
```